United States Patent [19]
Ishihara et al.

[11] Patent Number: 5,843,376
[45] Date of Patent: Dec. 1, 1998

[54] REACTION APPARATUS FOR AUTOMATIC ANALYSIS

[75] Inventors: Narihito Ishihara; Kiyofumi Yoshida; Hidechika Hayashi, all of Kanagawa, Japan

[73] Assignee: Tosoh Corporation, Yamaguchi, Japan

[21] Appl. No.: 761,939

[22] Filed: Dec. 9, 1996

[30] Foreign Application Priority Data

Jul. 24, 1996 [JP] Japan .................................. 8-194594
Dec. 13, 1996 [JP] Japan .................................. 7-324446

[51] Int. Cl.$^6$ .................................................. G01N 35/04
[52] U.S. Cl. .............................. 422/64; 422/63; 422/67; 422/104; 436/43; 436/47; 436/48; 198/778
[58] Field of Search .................................. 422/63, 64, 65, 422/104, 67; 436/43, 47, 48; 198/723, 724, 778

[56] References Cited

U.S. PATENT DOCUMENTS

| | | | |
|---|---|---|---|
| 1,910,241 | 5/1933 | Chapman | 198/778 |
| 2,873,019 | 2/1959 | Kay et al. | 198/778 |
| 4,163,643 | 8/1979 | Hunter et al. | 422/65 |
| 4,363,245 | 12/1982 | Schmid . | |
| 4,495,975 | 1/1985 | Harstrom et al. | 141/157 |
| 4,528,159 | 7/1985 | Liston | 422/65 |
| 4,838,453 | 6/1989 | Luckstead . | |
| 4,879,841 | 11/1989 | Sjostrand . | |

FOREIGN PATENT DOCUMENTS 2235859  1/1975  France .
3415873A1 10/1985 Germany .

Primary Examiner—Long V. Le
Attorney, Agent, or Firm—Sughrue, Mion, Zinn Macpeak & Seas, PLLC

[57] ABSTRACT

A reaction apparatus is provided which is suitable for automatic immunoassay equipment and is capable of conducting treatments in reaction vessels for different reaction conditions such as reaction time and treatment method like a one-step method and a two-step method. The apparatus comprises a conveying mechanism for conveying vessels containing a objective measurement substance around a rotation center. The conveying mechanism comprises a fixed disk 1 for guiding the vessels 5 along a spiral lane 2, and a rotation disk 3 for guiding the vessels 5 along radial lanes. The vessels 5 are inserted at intersection points of the spiral lane and the radial lanes, and are conveyed with the rotation of the radial lanes along the spiral lane. The mechanism is constituted such that the vessels 5 for long-time treatment and the vessels for short-time treatment are inserted to the same insertion position and the vessels 5 for short-time treatment is taken out from an intermediate way of the conveying route.

26 Claims, 13 Drawing Sheets

REACTION APPARATUS FOR AUTOMATIC ANALYSIS

BACKGROUND OF THE INVENTION

Field of the Invention

The present invention relates to a reaction apparatus for analysis of an objective substance by utilizing a chemical reaction or a biochemical reaction. Particularly, the present invention relates to a reaction apparatus suitable for automatic immunoassay of a trace amount of an objective substance in a biological sample contained in a vessel such as a blood sampler and a sample reaction vessel, for example, a liquid sample such as serum and urine, and a liquid extract obtained by extraction from a tissue or the like, by utilizing immune reaction.

The reaction apparatus of the present invention is described regarding application to automatic analysis of a trace amount of a substance by utilizing immune reaction as an example. Conventionally, such automatic analysis equipment comprises a reaction apparatus (an incubator) in which reaction vessels containing a sample and a reagent are brought into contact with a surface or an atmosphere kept at a constant temperature for a prescribed time to allow the reaction of the sample with the reagent to proceed successively under constant conditions. The system for the reaction (or incubation) includes a batch system in which the reaction vessel is fixed for a prescribed reaction time, and a conveyor system in which the reaction is allowed to proceed with the reaction vessel conveyed through the incubator.

In one method of the conveyor system, reaction vessels are hooked to an endless chain moving in a closed circuit in contact with a temperature-controlled surface, and are moved pitch by pitch at a prescribed time interval. In another method of the conveyor system, reaction vessels are placed on a turntable which is turned by a prescribed angle at a prescribed time interval. In any of the methods, the vessel delivery mechanism serves also as the incubator. In a still another method of the conveyor system, reaction vessels are immersed in a temperature-controlled water bath.

The automatic analysis by immunoassay frequently requires one or more hours of reaction time (incubation time). In such a long time of treatment, the incubator is required, for efficient treatment, to be capable of holding many reaction vessels simultaneously in a reaction state. For example, for obtaining measurement results every 30 seconds for series of one-hour reactions, at least 120 reaction vessels are required to be kept simultaneously in a reaction state.

Furthermore, the reaction apparatus is required to be smaller. In order to achieve miniaturization while satisfying the above conditions, the incubator is preferably capable of holding reaction vessels as compactly as possible.

For compact setting of the reaction vessels, the above batch system is more suitable in which the reaction vessels are fixed without movement in the incubator. However, such a batch system has the disadvantage that it is very difficult to keep the respective reaction vessels at the same temperature. Specifically, many reaction vessels cannot readily be controlled to have a consistent temperature in an incubation space technically. In the batch system, the temperature distributes inevitably in the space in the incubator to cause variation of the reaction conditions for respective reaction vessels. Thus the measurement accuracy is impaired by the positional difference. Further, in the case of a two-step method, intermediate washing is conducted by transferring the reaction vessel to the other unit or by bringing a washing device to the reaction vessel in the incubator. The mechanism for the transfer is required to be highly precise in positional registration, which is disadvantageous technically and economically.

On the other hand, the conveyor system in which the reaction is allowed to proceed with the reaction vessel being conveyed is advantageous in uniformity of the reaction conditions, since all the reaction vessel can be treated relatively easily with the same temperature hysteresis regardless of temperature distribution in the incubator by conveying all the reaction vessels along the same route. However, the temperature of the atmosphere should be controlled throughout the conveying range, so that the conveyor system having a linear conveying route needs an extremely large length of the incubator. The space efficiency can be improved in the aforementioned chain-conveying method of the conveyor system by curving the conveying path many times. However, the vessel-conveying mechanism having curved portions needs a sprocket for each curved portion, which requires many parts and complicates the conveying mechanism, and is disadvantageous in cost. The turntable method employing concentrical multiple conveying routes is not suitable for keeping all of the reaction vessel under the same reaction conditions in the same temperature hysteresis, whereas the turntable method employing vessel arrangement in one conveying circle circumference requires turntable of a large diameter, disadvantageously.

Further, a two-purpose reaction apparatus, for uses for a one-step method without intermediate washing and a two-step method with intermediate washing, requires additional ports including an intermediate washing port, a second immune reagent-dispensing port, a final washing port, and a detection port for assaying a marker or a product derived from a marker in combination with the reaction apparatus. The intermediate washing port and the final washing port requires respectively a vertical driving mechanism, a washing liquid supplying line, and a washing liquid discharge line. Therefore, the apparatus becomes duplicated and complicated to increase the apparatus production cost. Therefore, the production of the industrial two-purpose apparatus is restricted considerably.

SUMMARY OF THE INVENTION

An object of the present invention is to provide a reaction apparatus suitable for automatic analysis with high measurement accuracy in a small size without the above problems.

Another object of the present invention is to provide a reaction apparatus suitable for automatic immunoassay.

A further object of the present invention is to provide a reaction apparatus which is suitable for automatic analysis utilizing immunoassay, and is useful for conducting concurrent reactions of different protocols, such as one-step method and two-step method, without complication of the apparatus structure with high treatment efficiency. This object is explained specifically below. The reaction time is required in some cases to be changed, for example, 20 minutes, 40 minutes, and 60 minutes. In a certain one-step method of enzyme immunoassay, the protocol includes steps of reaction, B/F separation (washing), substrate dispensation, and fluorescence measurement, whereas in a certain two-step method, the protocol is different and includes steps of a first reaction, B/F separation, a second reagent dispensation, a second reaction, B/F separation, substrate dispensation, and fluorescence measurement. In a system of linear conveying of reaction vessels, the washing mechanism or the detection device is placed at the position where the reaction is completed, or the reaction vessels are transferred to another unit from the position where the reaction is completed to conduct washing or detection, whereby the number of the units become larger. For measurement for different reaction times, the conveying speed may be changed. However, if the conveying speed is lowered to meet the long reaction time, the number of measurements per unit time becomes less. Concurrent measurement of reactions of different reaction times or different protocols cannot be conducted without employing plural reaction lanes. Therefore, automatic analysis equipment is demanded which solves such problems.

A further object of the present invention is to provide automatic analysis equipment comprising a reaction apparatus in a small size as a whole with a small installation area.

The reaction apparatus for automatic analysis, especially of a biological sample of the present invention comprises a conveying mechanism to convey vessels containing an objective substance, especially of a biological sample, around a rotation center: the conveying mechanism comprising a first guiding means for guiding the vessels along a spiral lane provided spirally on a first horizontal plane, and a second guiding means for guiding the vessels along radial lanes provided radially on a second horizontal plane; the first guiding means and the second guiding means being placed concentrically and counterposed on different levels; the vessels being fixed into intersection points of the spiral lane and the radial lanes to control horizontal movement of the vessels by the spiral lane and the radial lanes; and the vessels being conveyed by rotation of at least one of the first guiding means and the second guiding means around the rotation center.

The radial lanes of the second guiding means are provided usually in a radial manner in plurality at constant angle intervals. The radial lane is usually in a shape of a slit perforating a disk or the like, but may be a groove.

DETAILED DESCRIPTION OF THE PREFERRED EMBODIMENT

Figure 1:
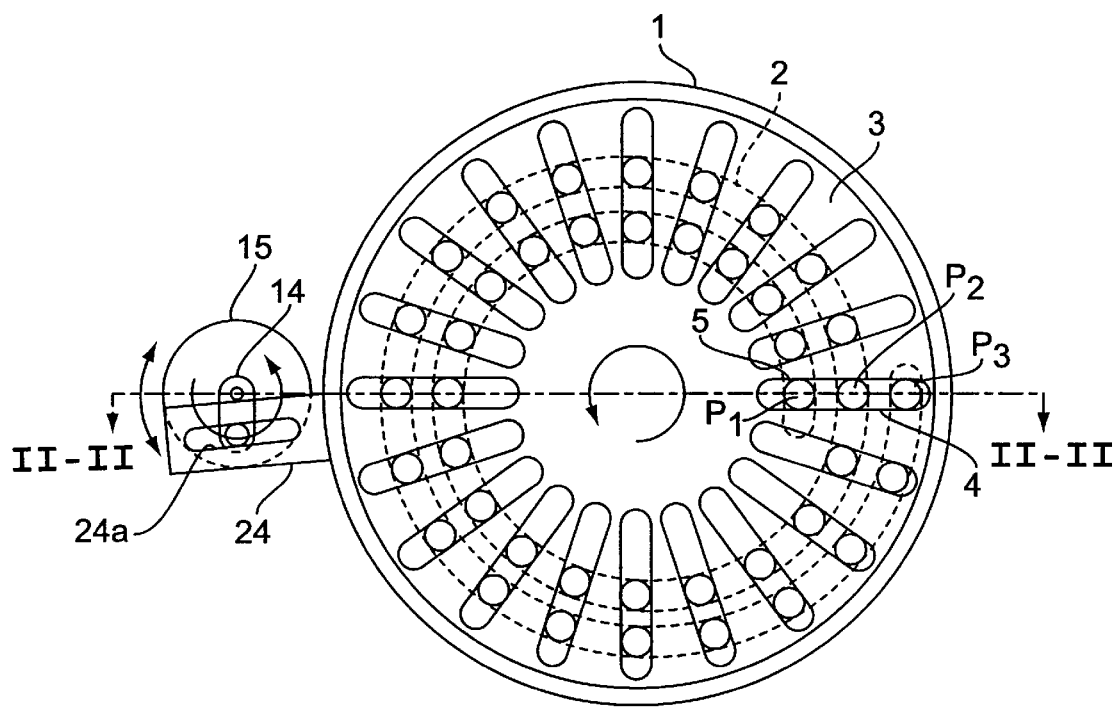
FIG. 1 is a plan view showing schematically the apparatus of First Embodiment of the present invention.

With the aforementioned constitution of the apparatus, the reaction vessel is conveyed along the radial lane of the second guiding means when the first guiding means is turned, while the reaction vessel is conveyed along the spiral lane of the first guiding means when the second guiding means is turned. The reaction vessel can be conveyed to any desired position by rotating the both guiding means. In particular, in the spiral conveying system, all of the reaction vessels are conveyed along the same route (namely, spiral lane) while the reaction proceeds in the respective vessels. Further, in the spiral system, the vessels are driven by the rotating plate (namely, turntable having radial lines) as the second guiding means. Therefore, the requirement for the miniaturization of the apparatus can be satisfied advantageously by conveying a number of reaction vessels on the same route provided in plural lines (a spiral lane) in a narrow radial range.

The first guiding means and the second guiding means are generally constructed from a circular planar pedestal, or a disk. For example, the first guiding means may be a fixed pedestal or a rotation plate placed horizontally, having a continuous spiral lane which may be a spiral groove or a spiral perforation hole. Generally the length of the spiral lane is preferably two or more rounds. In the spiral conveying system, the vessel moves inside or outside by one spiral pitch by one rotation of the second guiding means.

In the aforementioned constitution, the wording "the first guiding means and the second guiding means counterposed on different levels" signifies that the two guiding means are placed so as not to interfere the rotation of the rotating plate, for example, with a suitable interspace on the upper and lower levels with either one of the means placed on the upper level. Further, the first guide means or the second guide means may be provided in plurality on different levels. For example, the first guiding means are provided above and below the second guiding means, for example, in arrangement of (spiral lane)/(radial lane)/(spiral lane), or adversely the second guiding means are provided above and below the first guiding means in arrangement of (radial lane)/(spiral lane)/(radial lane). By fixing or synchronously rotating both of the plural same guiding means provided above and below, the play of the vessel held at the intersection of the lanes can be decreased effectively.

In a preferred constitution (as stated in claims 5, 6, and 10), the first guiding means is provided as a fixed pedestal or a fixed disk which has a spiral lane for receiving bottoms of the reaction vessels and for guiding the vessels spirally and may be made temperature-controllable, if necessary; and the second guiding means which has plural slits separately in the radial direction is provided above the fixed pedestal rotatably around the rotation axis positioned at the center of the lane spiral.

For example, in a vessel conveying mechanism, the rotation of the rotating plate to convey the reaction vessels can be controlled by a rotation drive-controlling means comprising a rotation mechanism such as a stepping motor, and a servomotor, and a control mechanism; the reaction vessels are held at the intersection points of the spiral lane and the radial lanes; and the reaction vessels are conveyed spirally by the rotation drive-controlling means. Usually the rotation drive is conducted intermittently for insertion and removal of the vessels.

In the constitution in which the rotating plate is placed lower, the rotating plate is preferably temperature-controllable to control the temperature of the liquid at the bottom of the reaction vessel. For temperature control of the fixed pedestal or the rotation plate, an electric heater is useful, but is not limited thereto. The temperature control of the rotating plate can be conducted by use of a slipping connector or a rotary connector for supplying electric power or temperature-control signals.

In the spiral conveying system, when the second guiding means employs a rotation plate for the guiding and is placed above the first guiding means, the radial lane may be a perforation hole (slit); and when the rotation plate is placed below the first guiding means, the radial lane may be either a perforation hole or a radial groove having a bottom. Similarly, when the first guiding means is a fixed pedestal or a fixed disk and is placed above the second guiding means, the lane may be a perforation hole (slit); and when the fixed pedestal or disk is placed below the second guiding means, the lane may be either a perforation hole or a radial groove having a bottom.

The reaction apparatus for automatic analysis of the present invention can be more highly automated by providing an insertion means for inserting the reaction vessels at the intersection points of the spiral lane and the radial lanes at prescribed radial and rotational positions, and a removal means for taking out the inserted reaction vessels from the intersection point at another prescribed radial and rotational position. When the apparatus is operated with the reaction vessels for different measurement items simultaneously, for example, different time lengths of reactions (e.g., 20 minutes, 40 minutes, and 60 minutes), or different protocols such as one-step and two-step immune reactions, the one insertion means or the one removal means is desired to be capable of working at plural positions. Thereby, the reaction vessels for one-step immune reaction and for two-step immune reaction can be treated concurrently. In such a case, the insertion means or the removal means is constructed preferably such that it moves linearly along the diameter line passing over the rotation center of the rotating disk between a predetermined vessel insertion position and a predetermined vessel removal position (as stated in claim 21). Thereby, a vertical movement mechanism or a vessel-holding mechanism (or vessel-sucking mechanism) can be moved to the vessel insertion position or the vessel removal position. For this purpose, the rotation disk is controlled to turn intermittently in one direction, and preferably is controllable so as to turn reversely or to turn at a rotation angle different from the normal intermittent driving, as necessary.

The reaction apparatus (incubator) having the aforementioned vessel-conveying mechanism may be combined with a sample-dispensing means for dispensing the sample into the reaction vessel, or a reagent-dispensing means for dispensing a reagent thereto in the preceding step before the vessel is inserted to the vessel-conveying mechanism. The apparatus may also be combined with a detector, a substrate-dispensing mechanism, a washing mechanism, or the like in the succeeding step after the vessel is removed from the vessel-conveying mechanism. Such means and the mechanisms for the preceding or succeeding steps may be equipped independently of the vessel-conveying mechanism, or equipped by utilizing the vessel-conveying mechanism.

For example, (as stated in claim 15) in a radially inner or outer side of the radial lane of the rotation disk placed at the upper level, plural vessel-holders are provided concentrically; the reaction vessels after the reaction are inserted thereto; and ports for a detector, a substrate dispensing mechanism, a washing mechanism, or the like may be equipped on the circulation route outside the periphery of the rotation disk. The structure of the vessel-holder may be of vertical perforation hole, or a recess, but is not specially limited thereto, provided that it can hold the vessel stably.

The vessel-holders are provided on a circle circumference of the rotation disk (usually on and along the periphery of the disk) constituting the second guiding means independently of the spiral lane, and the ports for a detector, a substrate-dispensing mechanism, a washing mechanism, and the like are provided on the route of the rotation. Thereby, the above treatments can be conducted on the rotation disk. Thus, the vessel-conveying mechanism can be used as the delivery means for necessary treatment after or during the incubation in the reaction apparatus. Thereby the automatic analysis equipment can be miniaturized, and the mechanism thereof can be simplified, advantageously. In the case where measurements of different reaction time lengths as mentioned above are concurrently conducted or where measurements of different protocols such as a one-step method and a two-step method are simultaneously conducted in the reaction apparatus; the treatments (washing, substrate dispensation, detection, etc.) for the separate reaction vessels taken out from the same slit have sometimes to be treated at the same time. In consideration of the simultaneous treatment, the vessel-holders are preferably provided in a number of (number of slits)×n, where n is an integer, and if two vessels taken out from the same one slit should be treated simultaneously, the integer n is equal to 2. Specifically, the vessel-holders include a first group of vessel holding racks which are provided at the radially outer side of each of the radial lanes, and a second group of vessel-holders which are respectively provided in each interval between the first-group racks. One first-group rack and one second-group rack are provided for each of the radial lanes to receive the vessels. In this case, for example, the first-group vessel-holders may be employed for longer-time treatment and the second-group vessel-holders may be employed for the shorter-time treatment, but the constitution of the holding racks is not limited thereto.

The content in the reaction vessel can be agitated without contact in the present invention, by placing a magnetic body in the reaction vessel and driving a magnetic means outside the vessel. A preferred magnetic means is an agitating plate having magnets arranged along the spiral lane and driven reciprocally in the rotation direction of the disk. The reciprocal movement of the agitating plate in nearly the spiral direction can be caused by moving the agitation plate reciprocally in a certain angle around the rotation center of the guiding member. For the magnetic agitation, preferably the reaction vessel is made of a nonmagnetic material, and the fixed pedestal and at least the board placed under the rotation plate are made nonmagnetic.

In a preferred constitution of the automatic analysis equipment employing the above-described reaction apparatus (as stated in claim 26), there may be equipped, below, above, or on the level of the reaction apparatus, a sample stocker for carrying containers containing an analysis sample arranged in a circle, or a dispensing means for dispensing a prescribed quantity of the samples to the reaction vessel. In another preferred constitution, there may be equipped, below, above, or on the level of the reaction apparatus, a reaction-vessel stocker having the reaction vessels to be delivered to the conveying mechanism in matrix or on shelves, and a delivering means for delivering the sample container from the reaction vessel stocker to the conveying mechanism in the reaction apparatus. In such a manner, the installation area of the automatic analysis equipment is remarkably reduced by utilizing the space three-dimensionally.

With the aforementioned constitution, for example, in a spiral conveying system, when the reaction vessels after the addition of the sample and the reagent are set at the intersection points of the innermost or outermost portion of the spiral lane and the radial lanes, the reaction vessels are conveyed on a route resulting from the sum of the rotational (spiral) movement and the radial movement of the reaction vessel, thus all the reaction vessels are conveyed on the same route effectively in a small space.

When the length of the spiral lane is two rounds or more (720° or more), and if the rotation plate is rotated at a rate of 20 minutes per rotation, then two cycles of rotation takes 40 minutes, and different reaction times can be selectively given to the respective reaction vessel only by changing the radial position (time) for the removal of the vessel. In this case, the apparatus can be constituted such that the reaction vessels are taken out at the same rotation angle position, whereby one removal means is enough which has a linear scanning movement mechanism and is relatively simple. As described above, the reaction times can be varied for the respective reaction vessel by changing the position of removal of the reaction vessel. Alternatively, the reaction time can also be varied by changing the positions of insertion of the reaction vessel with the removal position being unchanged.

In still another example, outside the radial lanes (slits) of the rotation plate, vessel-holders are arranged for holding the reaction vessel concentrically with the rotation plate, and a washing mechanism, a detector, or the like are provided on the circulation route of the vessel-holders; and the reaction vessels after completion of the reaction are transferred to the vessel-holders. Thereby, the washing treatment and the detection treatment can be conducted on the same vessel-conveying mechanism, enabling simplification of the entire unit.

Further, in an embodiment, in which reaction vessels for different protocols, for example a one-step method and a two-step method, are placed simultaneously in the same apparatus, intermediate washing in the two-step method is conducted by bringing the reaction vessel for washing to a vessel-holder of the second group, conducting washing there, and returning the vessel to the original radial lane (slit). Thereby, the vessel-holders of the first group may be employed for treatments of from final washing to detection for both the one-step method and the two-step method without any trouble. When vessels of different reaction time of measurement are placed in the same apparatus, the vessels can be treated by utilizing the vessel-holders of the second group. The concurrent treatment of different measurement items mentioned here includes measurement by different protocols, measurement in different times, measurement by different protocols in different times, and so forth.

The reaction apparatus of the present invention can be employed suitably as automatic analysis equipment for detecting or measuring an objective substance by causing reaction in a prescribed time. The detected or measured matter may be any of the objective substance itself, a labelled compound (e.g., a fluorescent substance) derived by labelling the objective substance, and a substance produced from the labelled compound (e.g., a fluorescent substance produced by a labelled enzyme). The reaction in the reaction apparatus is not specially limited, but the apparatus is particularly suitable for immune reactions. Typically, the reaction may be a one-step method or a two-step method in which an enzyme is employed as the labelling agent, an antibody for the objective biological substance is labelled by the enzyme, and then it is deposited onto a solid surface to form a complex.

The embodiments of the present invention is described below.

Embodiment 1

Figure 2:
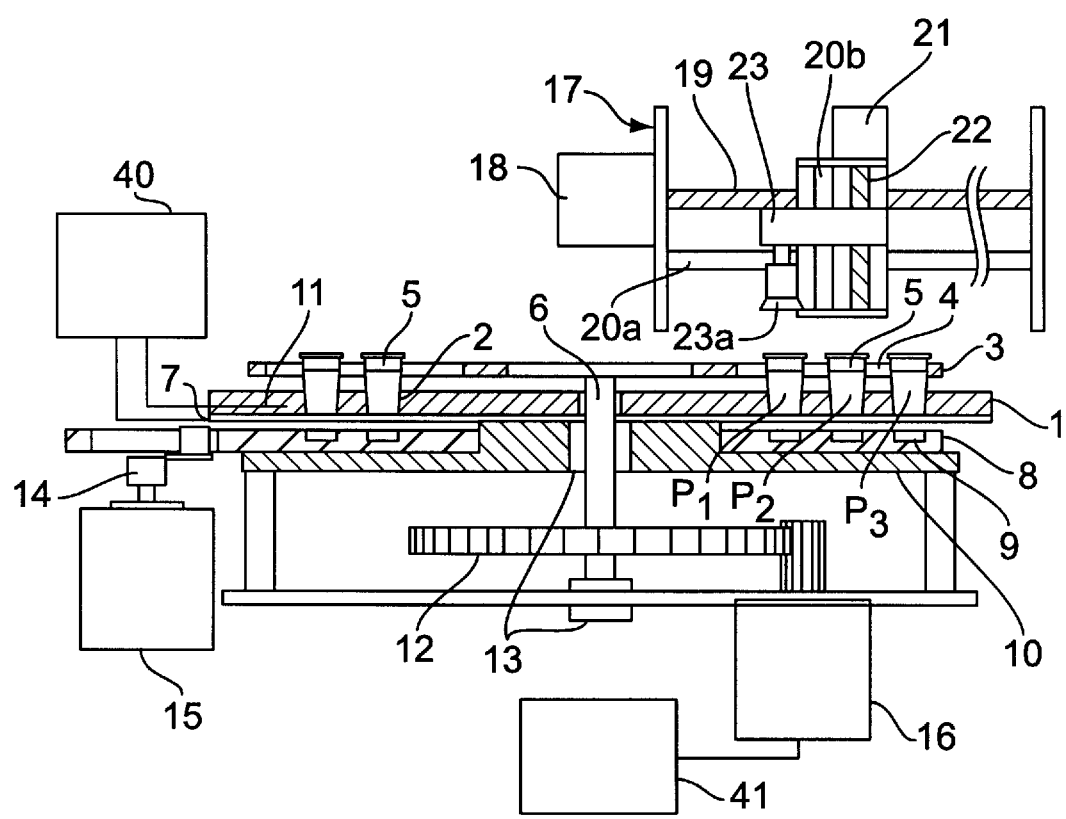
FIG. 2 is a vertical sectional view of the apparatus of First Embodiment of the present invention.

FIG. 1 is a plan view of a reaction apparatus (incubator) of this embodiment. FIG. 2 is a sectional view taken on line II—II in FIG. 1.

In the drawings, a fixed plate 1 is in a shape of a horizontal disk as the aforementioned first guiding means, and is fixed and supported by the lower supporting plate 10 together with a sheet-shaped heater 7 provided on the entire lower face thereof. A temperature sensor 11 is provided at the lateral face of the fixed plate to monitor and control the temperature of the fixed plate 1 by a temperature controller 40. On the upper face of the fixed plate 1, a continuous spiral groove (spiral lane) 2 is provided which is in a spiral shape and has a width slightly larger than a reaction vessel 5. The spiral groove 2 has a length of about two rounds (720°) in this embodiment.

Above the fixed plate 1, a rotation plate 3 as the second guiding means is provided to be rotatable horizontally relative to the fixed plate 1. On this rotation plate 3, twenty slits (radial lanes) 4 are formed extending separately from the center in a radial direction in a constant radial angle with a width slightly larger than the size of the reaction vessels. An axis body 6 at the center of the rotation plate 3 is supported by a bearing 13, and the rotation of the motor 16 is transmitted to the rotation plate 3 through the gear 12 provided on the axis body 6. A stepping motor is employed as the motor 16 to control readily the rotation angle. The motor is controlled by a motor controller 41 to move intermittently to stop at prescribed rotation angle In this embodiment, non-contact agitation mechanism is provided by employing magnets to shorten the reaction time and uniformize the reaction. Specifically, the fixed plate 1 is made of a nonmagnetic material, and under the fixed plate 1, an agitation plate 8 is provided which is in an annular plate shape and has magnets 9 arranged along the spiral groove 2. A cam 14 which is connected to the driving axis of a shaking motor 15 is loosely fitted to a long hole 24a of a shaking arm 24 attached to the agitation plate 8. The agitation plate 8 is moved rotationally and reciprocally by a certain angle by the rotation of the cam 14. With the apparatus having the above construction, magnetic particles (not shown in the drawings) added into the reaction vessel 5 move reciprocally in accordance with the reciprocal movement of the agitation plate 8, thus the liquid containing the sample and the reagent being agitated to allow the reaction to proceed efficiently. The magnets 9 are preferably arranged under the reaction vessels 5. The magnets in this embodiment are arranged under the spiral.

In the above construction in this embodiment, a reaction vessel 5 inserted to the position $P_1$ at the intersection point of the spiral 2 and the radial slit 4 as shown in FIG. 1 is conveyed slowly with rotation of the rotation plate in spiral radially outward along the slit 4. When the rotation plate 3 has rotated by 360°, the reaction vessel 5 reaches the position $P_2$ in FIG. 1, and further when the rotation plate 3 has rotated by 720°, the reaction vessel 5 reaches the position $P_3$ shown in FIG. 1.

Accordingly, the reaction vessels delivered successively to the position $P_1$ are conveyed constantly along the spiral conveying route for a prescribed time, whereby the incubation is conducted at a constant temperature maintained by the fixed plate 1 controlled by a heater 7.

The numeral 17 indicates an insertion-removal mechanism for inserting the reaction vessels 5 to the aforementioned vessel conveying mechanism and removing them from the mechanism. In this embodiment, a sucking-pad support 23 having a sucking pad 23a for hanging up the reaction vessel 5 is controlled to move horizontally and vertically to insert and remove the reaction vessel at positions inside and outside the vessel-conveying mechanism. More specifically, a horizontal feeding mechanism is constituted of a horizontal feeding screw 19 driven by a stepping motor 18, and a guide shaft 20a, and a vertical feeding mechanism is constituted of a vertical feeding screw 22 driven by a stepping motor 21, and a guide shaft 20b. The feeding mechanism controls the horizontal and vertical movement of the sucking-pad support 23.

Figure 3:
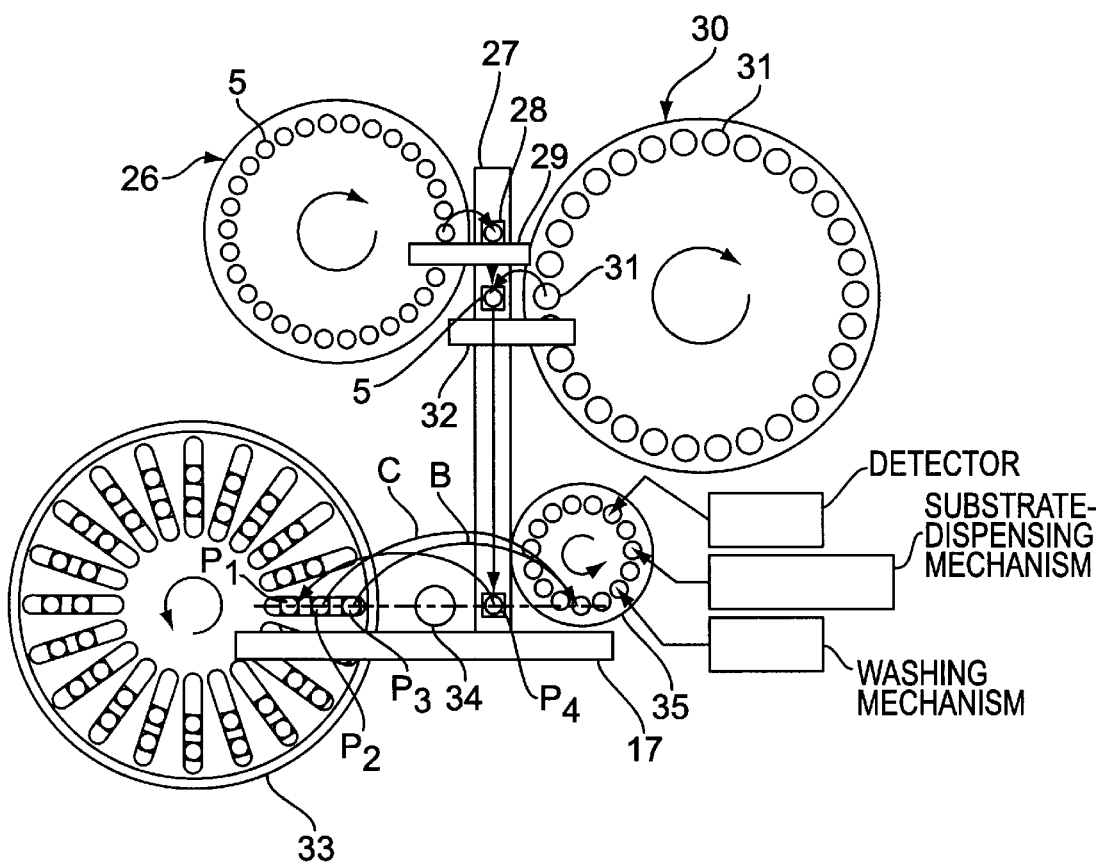
FIG. 3 illustrates schematically an example of an automatic analysis equipment system comprising the reaction apparatus of First Embodiment of the present invention.

FIG. 3 illustrate schematically an automatic analysis equipment system comprising the reaction apparatus (incubator) 33 described above by reference to FIGS. 1 and 2.

In the equipment shown in FIG. 3, a reaction vessel stocker 26 of a turntable type holds reaction vessels in which a magnetic body is contained. The reaction vessels 5 are taken out and transferred one by one from the reaction vessel stocker 26 to a delivery shuttle 28 by a vessel transfer mechanism 29 (detailed description is omitted here). This vessel transfer mechanism may be of the same type as the above-mentioned insertion-removal mechanism 17. The delivery mechanism for the vessels, selected according to the measurement items, onto the vessel-holders on the periphery of the reaction vessel stocker 26 is not explained here, since it is not an essential matter of the present invention. However, this mechanism is constituted such that the vessels for the intended measurement items are sequentially delivered.

Then, in this embodiment, the delivery shuttle 28 of the delivery shuttle mechanism 27 is once stopped in front of the turntable type sample stocker 30 holding sample containers 31. The sample is dispensed respectively from the sample container 31 to the reaction vessel 5 on the delivery shuttle 28 by a known suitable dispensing mechanism 32.

The sample vessel 5 having received the dispensed sample is delivered further by the delivery shuttle 28, and stops at the position $P_4$. There the sample vessel 5 is inserted as a reaction vessel 5 to an intersection point $P_1$ of the innermost round of the spiral groove 2 and a slit 4 by means of the aforementioned insertion-removal mechanism 17.

In the reaction apparatus (incubator) 33, the rotation plate 3 is controlled to turn in a counterclockwise direction as shown in FIG. 3 intermittently by one angle pitch of slits 4 every minute. The rotation plate is rotated in one cycle in 20 minutes, whereby the vessel is moved outside (or inside) by one spiral line pitch. Thereby, the vessel after reaction for 20 minutes and the vessel after reaction for 40 minutes come respectively to at the positions $P_2$ and $P_3$ in the same radial direction (Line A—A in FIG. 1.

The reaction vessel 5 after reaction of a prescribed time is transferred, in this embodiment, by the insertion-removal mechanism 17 to a turntable 35 equipped with a cleaning mechanism, a substrate-dispensing mechanism, and a detector, and treated for detection by the detector. The reaction vessel 5 after the detection is discarded into a discarding hole 34 by the same insertion-removal mechanism 17.

The treatment speeds of the washing mechanism, the substrate-dispensing mechanism, and the detector are set depending on the incubation treatment speed. When the samples of different reaction times, for example a sample removed from the 20-minute position $P_2$ (removal operation C in FIG. 3) and another sample removed from the 40-minute position $P_3$ (removal operation B in FIG. 3) are treated according to the measurement items, the samples can be treated without lowering the treatment performance of the incubator by raising the treatment speed per unit time twice as that of the incubator.

Embodiment 2

Figure 4:
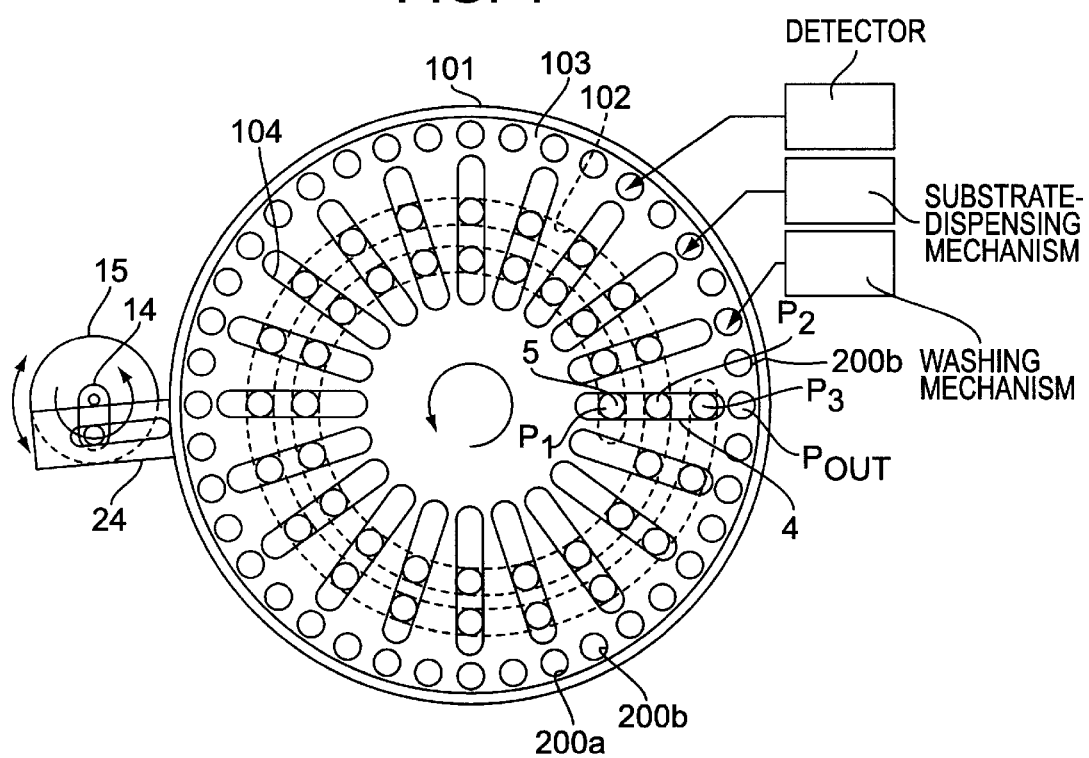
FIG. 4 is a plan view showing schematically of the apparatus of Second Embodiment of the present invention.
Figure 5:
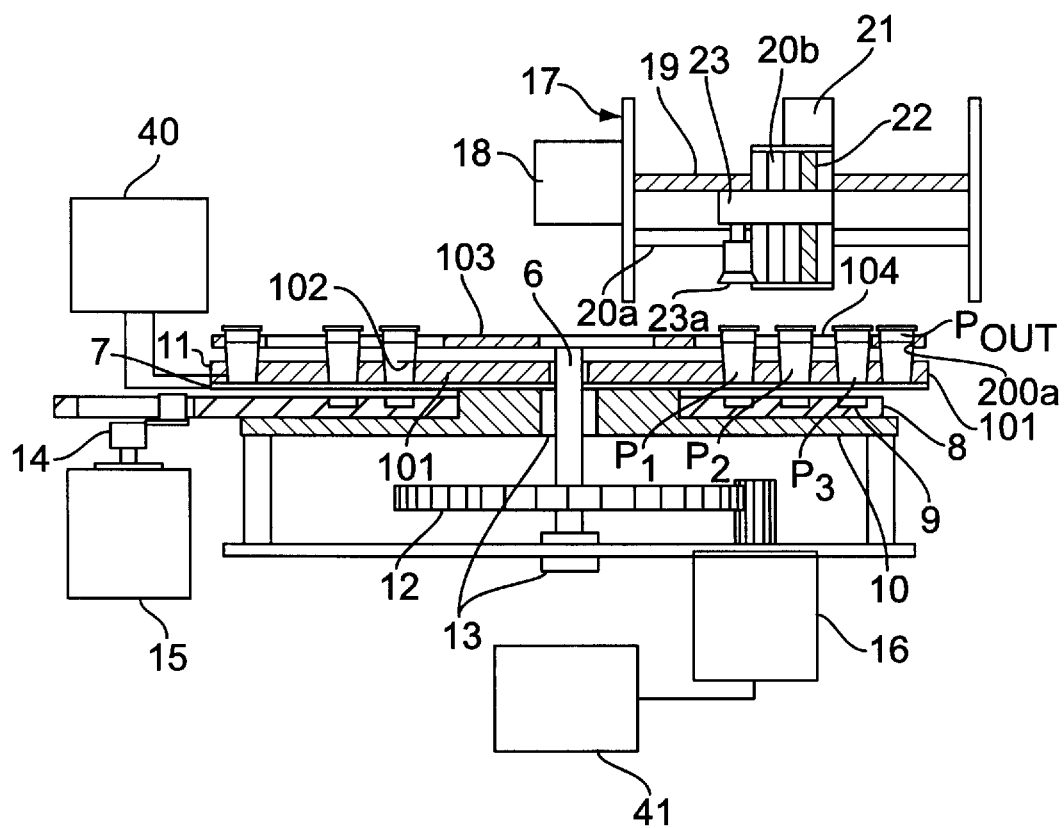
FIG. 5 is a vertical sectional view of the apparatus of Second Embodiment of the present invention.
Figure 6:
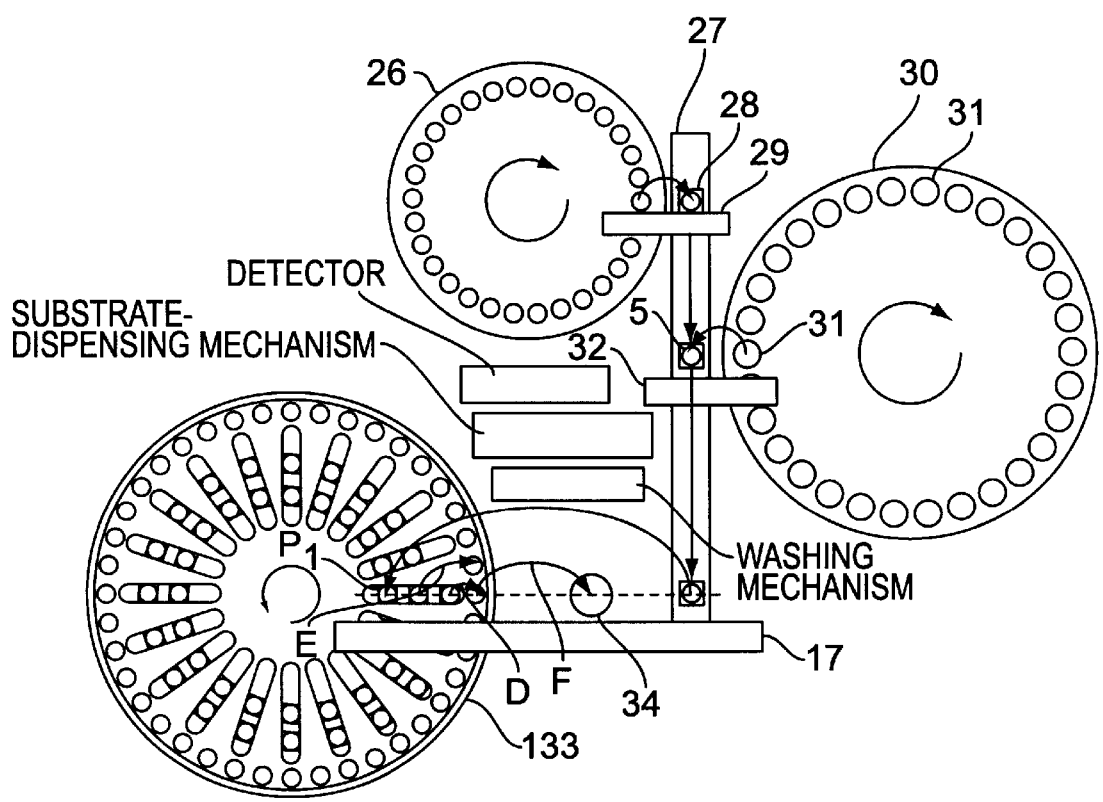
FIG. 6 illustrates schematically an example of automatic analysis equipment system comprising the reaction apparatus of Second Embodiment of the present invention.

FIGS. 4–6 shows an example of a reaction apparatus 133 in which vessel-holding holes (vessel-holders) 200a, 200b for reaction vessels 5 are provided concyclically on the periphery of a rotation plate 103 equivalent to the rotation plate 3 in FIG. 1 of Embodiment 1. Corresponding thereto, a streak of circular groove 104 is provided to make uniform the height of the reaction vessels 5 mounted on the spiral groove 2 on a fixed plate 101. The constitution is the same in other points as in the apparatus shown in FIGS. 1–3, so that the same reference numerals as in FIGS. 1–3 are used without explanation. The vessel-holding holes 200a, 200b are formed on the rotation plate 103 in such a dimension that the vessels 5 can be held by the hole without play.

In this Embodiment, the vessel holding holes 200a, 200b are provided on the periphery of the rotation plate 103; the washing mechanism, the substrate-dispensing mechanism, and the detector are arranged successively along the movement route of the vessel-holding holes 200a, 200b as shown in FIG. 4; and the treatment of detection is conducted for the reaction vessel delivered to the position by the rotation of the rotation plate 103.

FIG. 6 illustrates schematically the entire of the automatic analysis equipment having the reaction apparatus 133 of the constitution as shown in FIG. 5. This automatic apparatus is different from the one in FIG. 3 in that the vessel-holding holes 200a, 200b for holding the reaction vessels 5 are provided on the periphery of the rotation plates 103, and the washing mechanism, the substrate dispensing mechanism and the detector are equipped on the delivery route of the vessel-holding holes 200a, 200b, thereby rendering the turntable 35 unnecessary.

This embodiment shows an apparatus capable of conducting measurements for items requiring different reaction times (e.g., 20 minutes and 40 minutes). This apparatus has twenty slits 4, and forty vessel-holding holes 200a, 200b, which is twice the number of the slits 4, in a constant pitch at the positions radially outside the slits, and the rotation plate 103 is turned intermittently by one pitch (1/40 cycle of rotation, namely, by 9°), taking 20 minutes for one rotation.

Figure 7:
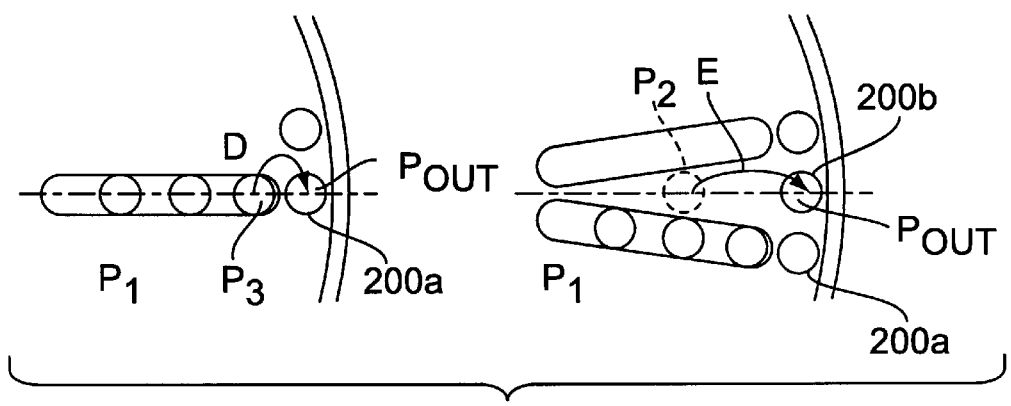
FIG. 7 illustrates the movement of the reaction vessel in transfer from a slit to a vessel-holding hole.

In the case where the measurement item includes 20-minute measurement and 40-minute measurement, two reaction vessels 5, 5 in which the reaction has been completed respectively are brought to the positions $P_2$ and $P_3$. A first reaction vessel (in position $P_3$ after 40-minute treatment) is transferred to a vessel-holding hole 200a at the position of $P_{out}$ (operation D in FIGS. 6 and 7). Then another reaction vessel (in position $P_2$ after 20-minute treatment) is transferred to a vessel-holding hole 200b at the position of Pout (operation E in FIGS. 6 and 7) radially outside the slit 104 and between the two vessel-holding holes 200a. The transferred reaction vessels 5 are delivered to the positions below a washing mechanism, a substrate dispensing mechanism, and a detector sequentially to be treated. The reaction vessels 5 after the measurement are discarded into a waste bucket 34 after nearly one rotation of the rotating plate.

In the above constitution, since the rotation plate 103 rotates in a 20-minute cycle or by one pitch in 0.5 minute, the measurement system is constituted so as to complete the steps of the sample dispensing, the washing, and the detection respectively within 0.5 minute.

With the above constitution, the separate turntable for the washing, substrate-dispensing, and detection can be omitted to miniaturize effectively the automatic analysis equipment (particularly automatic immunoassay equipment) employing the reaction apparatus.

For further miniaturization, the turntable constituting the sample stocker 30 is preferably arranged under the reaction apparatus 133 to utilize the space three-dimensionally to decrease the area occupied by the apparatus. The type of the reaction vessel stocker 26 is not limited to the turntable type, but may be a shelf type having shelves corresponding in number to the measurement item numbers.

Embodiment 3

Figure 8A:
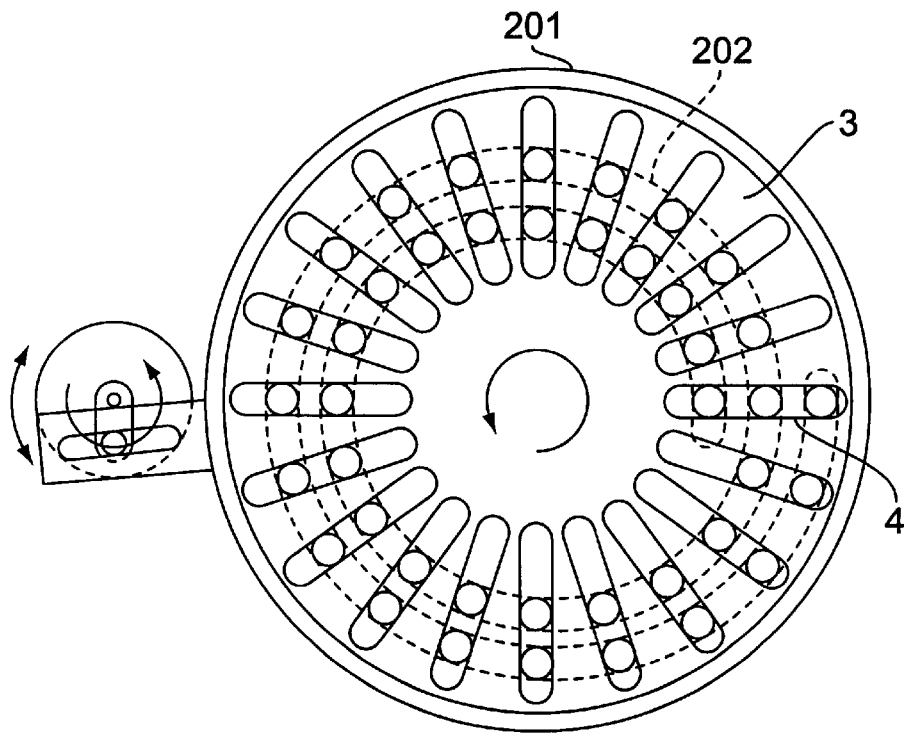
FIG. 8A is a plan view and FIG. 8B is a vertical sectional view, showing schematically the apparatus of Third Embodiment of the present invention.
Figure 8B:
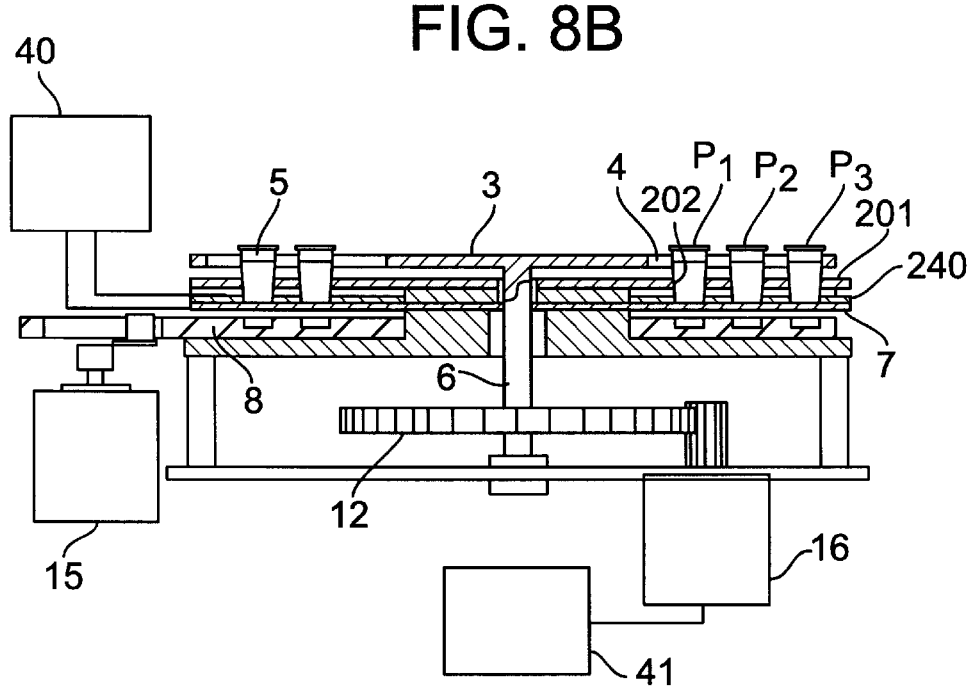

This embodiment as shown in FIGS. 8A and 8B is characteristic in comparison with Embodiment 1 in that the fixed plate 1 as the first guiding means as shown in FIGS. 1 and 2 is changed to a fixed disk 201 having a vertically perforated spiral lane 202; the bottoms of the reaction vessels 5 at the intersection points of the slits 4 as the radial lanes of the second guiding means and the above spiral lane 202 are allowed to slide on an upper face of a planar fixed disk 240 equipped with an electrical heater 7 at the reverse face thereof.

The constitution is the same in other parts as that shown in FIGS. 1 and 2, and the same reference numerals are used without explanation to simplify the description.

In the constitution of this embodiment, the spiral lane 202 is a vertical perforation hole, not of a groove structure, being readily cleanable, and not causing a trouble by a foreign matter entering the groove in vessel delivery, advantageously.

Embodiment 4

Figure 9A:
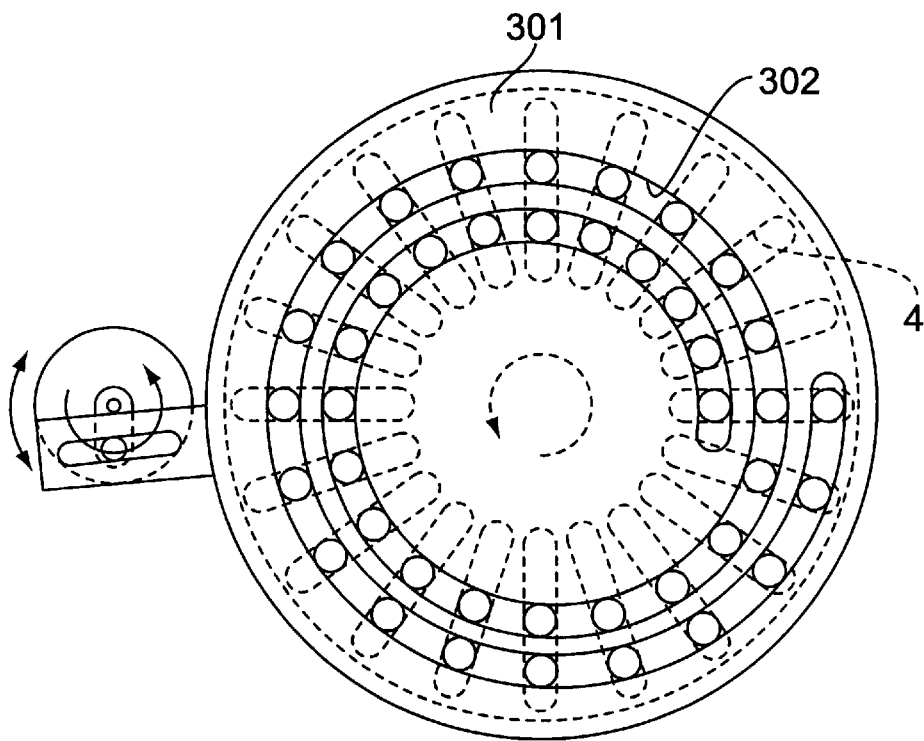
FIG. 9A is a plan view and FIG. 9B is a vertical sectional view, showing schematically the apparatus of Fourth Embodiment of the present invention.
Figure 9B:
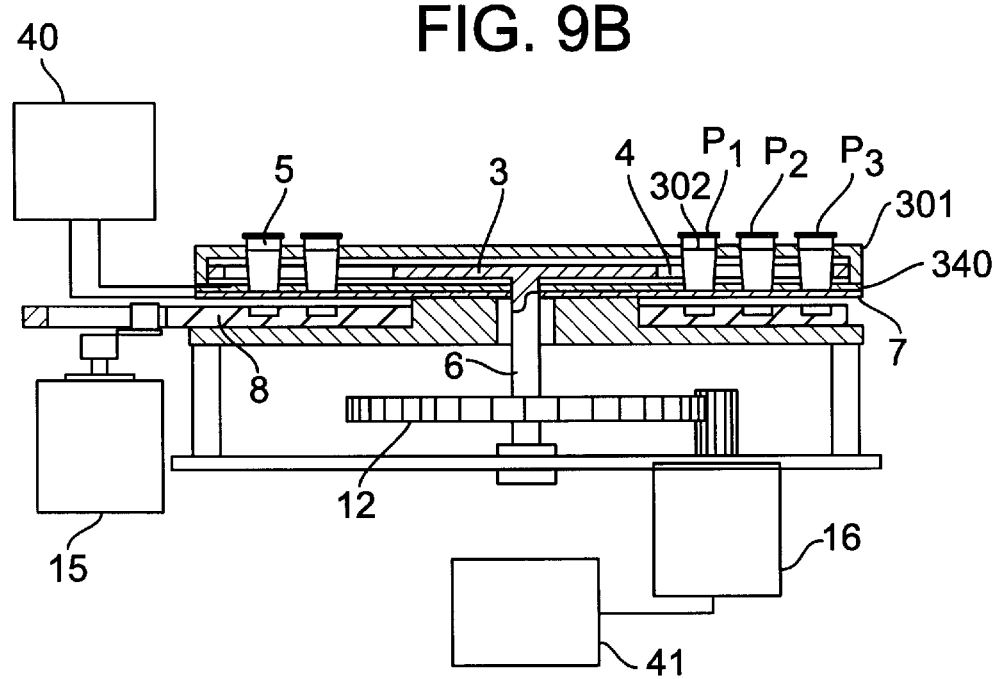
Figure 10:
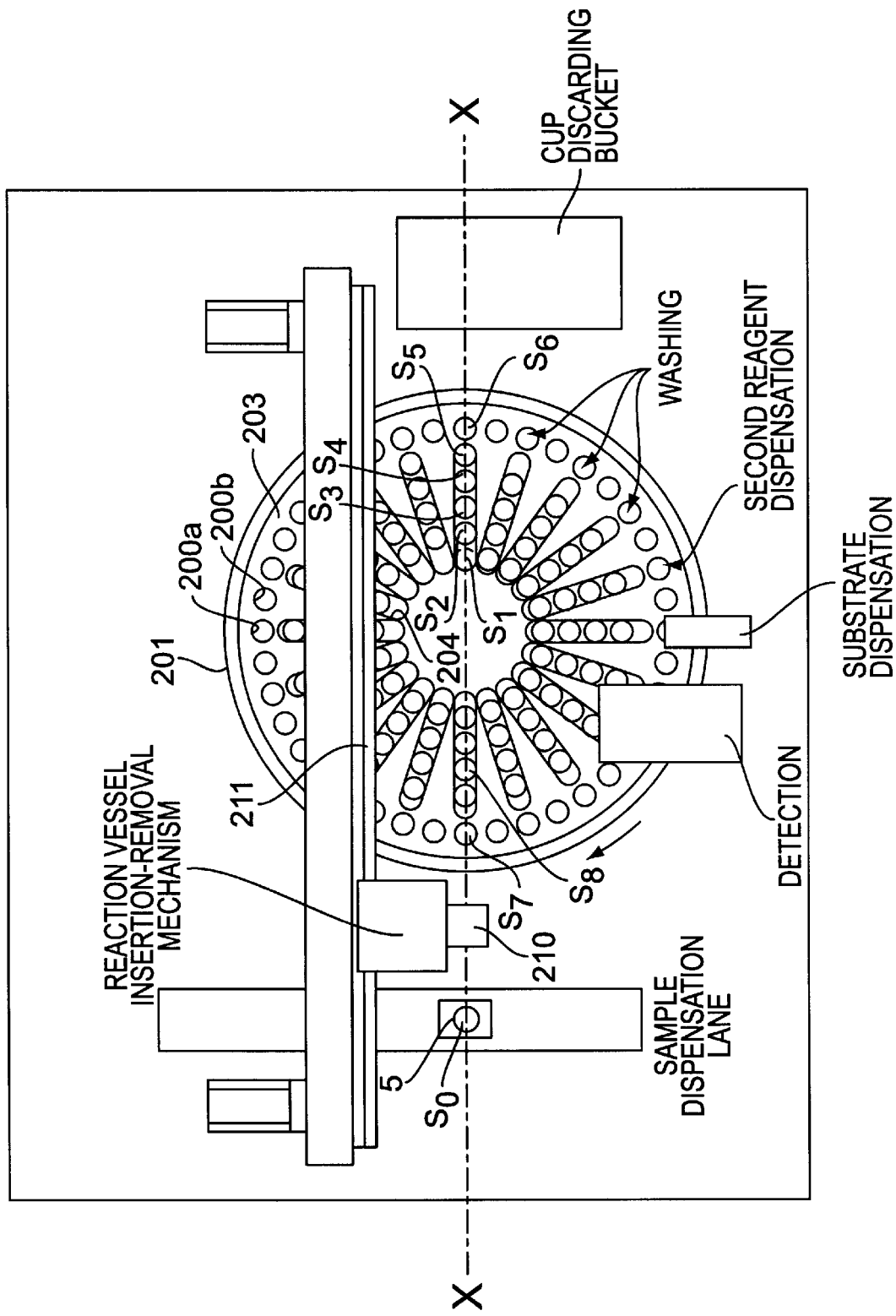
FIG. 10 illustrates schematically an example of automatic analysis equipment system comprising the reaction apparatus of Fifth Embodiment of the present invention.

This embodiment as shown in FIGS. 9A and 9B is characteristic in comparison with Embodiment 1 in that the fixed plate 1 as the first guiding means as shown in FIGS. 1 and 2 is changed to a fixed disk 301 having a vertically perforated spiral lane 302 and is placed above the rotation disk 3 having slits 4; the bottoms of the reaction vessels 5 at the intersection points of the slits 4 as the radial lanes of the second guiding means and the aforementioned spiral lane 302 are allowed to slide on an upper face of a planar fixed disk 340 equipped with an electrical heater 7 at the reverse face thereof. In this constitution, a means may be provided which prevents rotation of the fixed disk 301 placed above as necessary.

The constitution is the same in other parts as that shown in FIGS. 1 and 2, and by the same reference numerals are used without explanation to simplify the description.

In the constitution of this embodiment, the same effect can be obtained as in Embodiment 3.

Embodiment 5

FIGS. 10–14 illustrates preferred constitution and operation of automatic analysis equipment for enzymatic immunoassay. The equipment employs a reaction apparatus having the same constitution as that of Embodiment 2 having vessel-holding holes 200a, 200b at the portions radially outside the slit on the rotation disk.

In this embodiment, a delivery mechanism is constituted from a fixed disk 201 (see FIG. 8) having a vertically perforated spiral lane, and a rotation disk 203, placed above it and having twenty slits 204 as the radial lanes. At the radially outer side of the slits 204 on the rotation disk 203, there are provided a first group of vessel-holding holes 200a on the extension lines of the slits, and a second group of the vessel-holding holes 200b between the vessel holding holes 200a of the first group. The rotation disk 203 turns intermittently by one pitch in principle (18° in this embodiment) clockwise as shown by the arrow mark in the drawing. Thereby, the reaction vessels 5 inserted at the intersection points of the spiral lane and the slits revolute to move to the next outer lane of the spiral by one rotation cycle of the disk. Such constitution and delivery operation are the same as in Embodiment 2 described by reference to FIGS. 4–6.

In this embodiment, twenty slits 204 are provided as the radial lanes, and the spiral lane is provided in about four rounds (1440°) with some marginal length (for example, a marginal length for 180° rotation at the beginning point or the terminal point of the 1440° rotation. The rotation disk 203 is allowed to turn intermittently to complete one rotation cycle in 10 minutes.

The line X—X in the drawings indicates the scanning line of the vessel insertion-removal mechanism 210 provided to move along a rail 211 on the diameter line of the rotation disk. Into a reaction vessel 5, a reaction reagent is added and an objective sample is dispensed on a sample dispensation lane 212 (the dispensing means is not shown in the drawing). Then the reaction vessel 5 is pulled up at the position So by a lifting means (not shown in the drawing) of a nipping type provided at the lower portion of a head of a vessel insertion-removal mechanism. The head is moved along the line X—X to a position above insertion position $S_1$. There the reaction vessel 5 is lowered and inserted to the intersection point of the spiral lane and the slit 204. This operation is conducted every time when the rotation disk 204 is turned intermittently by one unit (18°). Thereby, 20 reaction vessels 5 are delivered in one round, and 80 reaction vessels are delivered in four rounds continuously.

Figure 11:
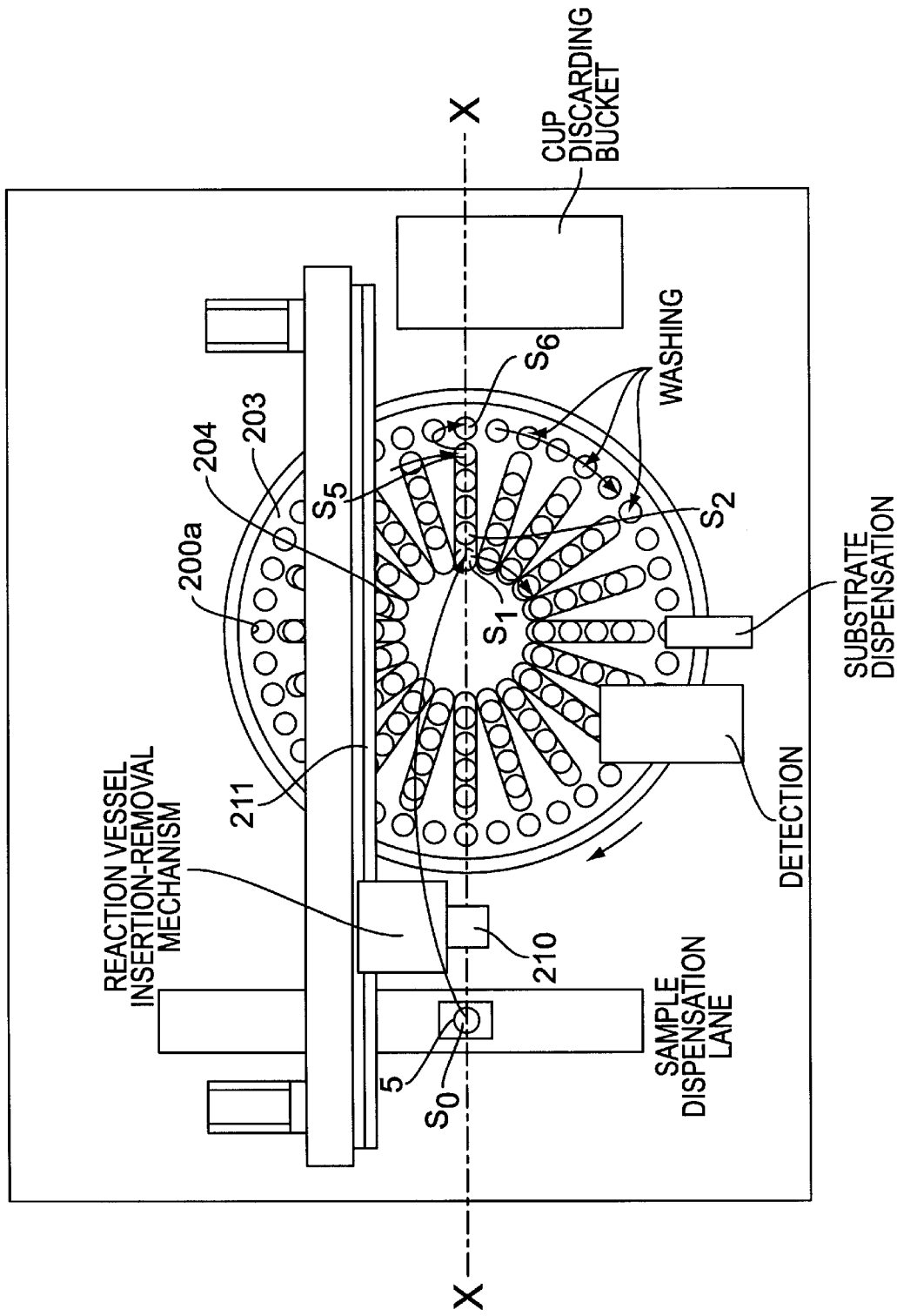
FIG. 11 illustrates movement of a reaction vessel in the apparatus of FIG. 10 in one-step treatment in 40 minutes.

The reaction vessel 5 for one 40-minute step is conveyed by four rotation cycles of the rotation disk to a position $S_5$, and is taken out (lifted), moved along the line X—X to a position $S_6$ by the insertion-removal mechanism 210, and inserted into a vessel-holding hole 200 (see FIG. 11). The reaction vessel 5 for one 20-minute step is taken out at the two round position $S_3$ in the same manner, and is inserted to the vessel holding hole 200b when the hole 200b has come to the position $S_6$ by turning of the rotation disk 203 by ½ pitch, namely 9° (see FIG. 12).

By the above operations, the reaction vessels are transferred to the vessel-holding holes 200a, 200b provided concyclically along the circumference of the rotation disk 203, and are subjected to treatments for washing, substrate-dispensation, and detection by the mechanisms placed along the circulation route of the vessel-holding holes moving with the rotation disk 203. Then the reaction vessels are conveyed to a position $S_7$ or $S_6$ by the rotation of the disk, taken out (lifted) by the vessel insertion-removal mechanism 210, and discarded into a cup discard bucket.

Figure 12:
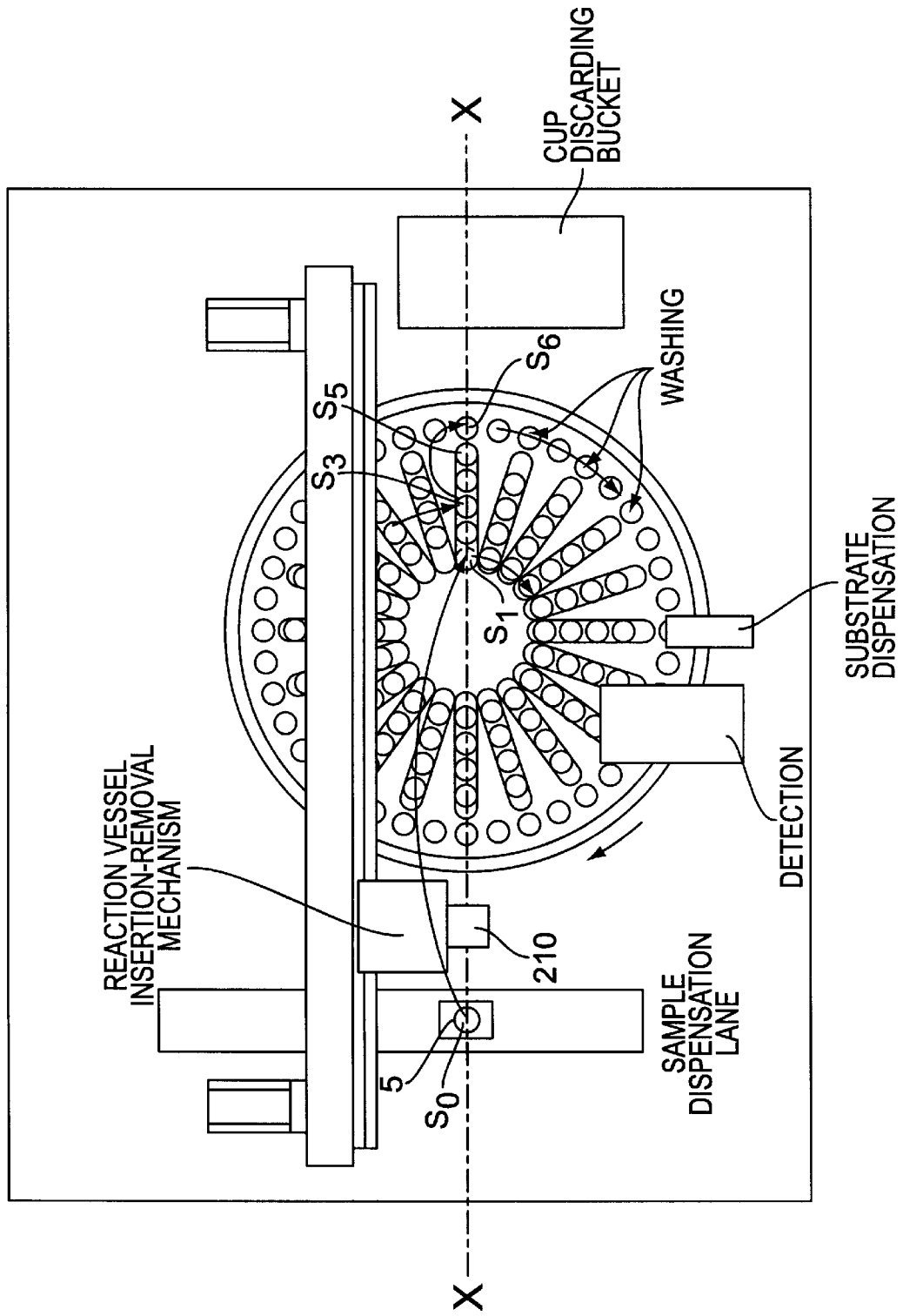
FIG. 12 illustrates movement of a reaction vessel in the apparatus of FIG. 10 in one-step treatment in 20 minutes.

In the case where the reaction vessels of different reaction time lengths are simultaneously placed on the disk as shown in FIG. 11 and FIG. 12, the respective reaction vessels are treated by utilizing the vessel-holding holes 200a of the first group for a 40-minute reaction and the ones 200b of the second group for the a 20-minute reaction.

On the other hand, in two 40-minute step reactions, the reaction vessel 5 is picked up when it has been conveyed to the two-round position $S_3$ in the same manner as above; the rotation disk 203 is turned by a ½ unit and the reaction vessel is inserted to the vessel-holding hole 200b which has come to the position $S_6$; washing treatment is conducted and a second reagent is dispensed; the reaction vessel 5 is returned from the position $S_6$ to the position $S_3$ in the slit, or the disk is turned in the normal rotation direction further after the second reagent dispensation; and the reaction vessel is returned from the position $S_7$ to the position $S_8$. Thereafter the treatment is conducted in the same manner as in the aforementioned one 40-minute step treatment.

FIG. 11 illustrates the operation of only a one 40-minute step treatment by the movement of the reaction vessel. The reaction vessel inserted to the position $S_1$ is conveyed to the position $S_5$ by four rotations of the disk. At this point of time, the reaction vessel is transferred to the vessel-holding hole 200a (or the vessel-holding hole 200b) at the position $S_6$. There the treatments of washing, substrate dispensation, and detection are conducted.

FIG. 12 illustrates the operation of only a one 20-minute step treatment by the movement of the reaction vessel. The reaction vessel inserted to the position $S_1$ is conveyed to the position $S_3$ by two rotations of the disk. At this point of time, the reaction vessel is transferred to the vessel-holding hole 200a (or the vessel-holding hole 200b). There the treatments of washing, substrate dispensation, and detection are conducted. Incidentally, to practice one 10-minute step treatment, the reaction vessel is taken out at the position $S_2$ by one rotation of the disk, and is transferred to the vessel-holding hole 200a (or 200b).

Figure 13:
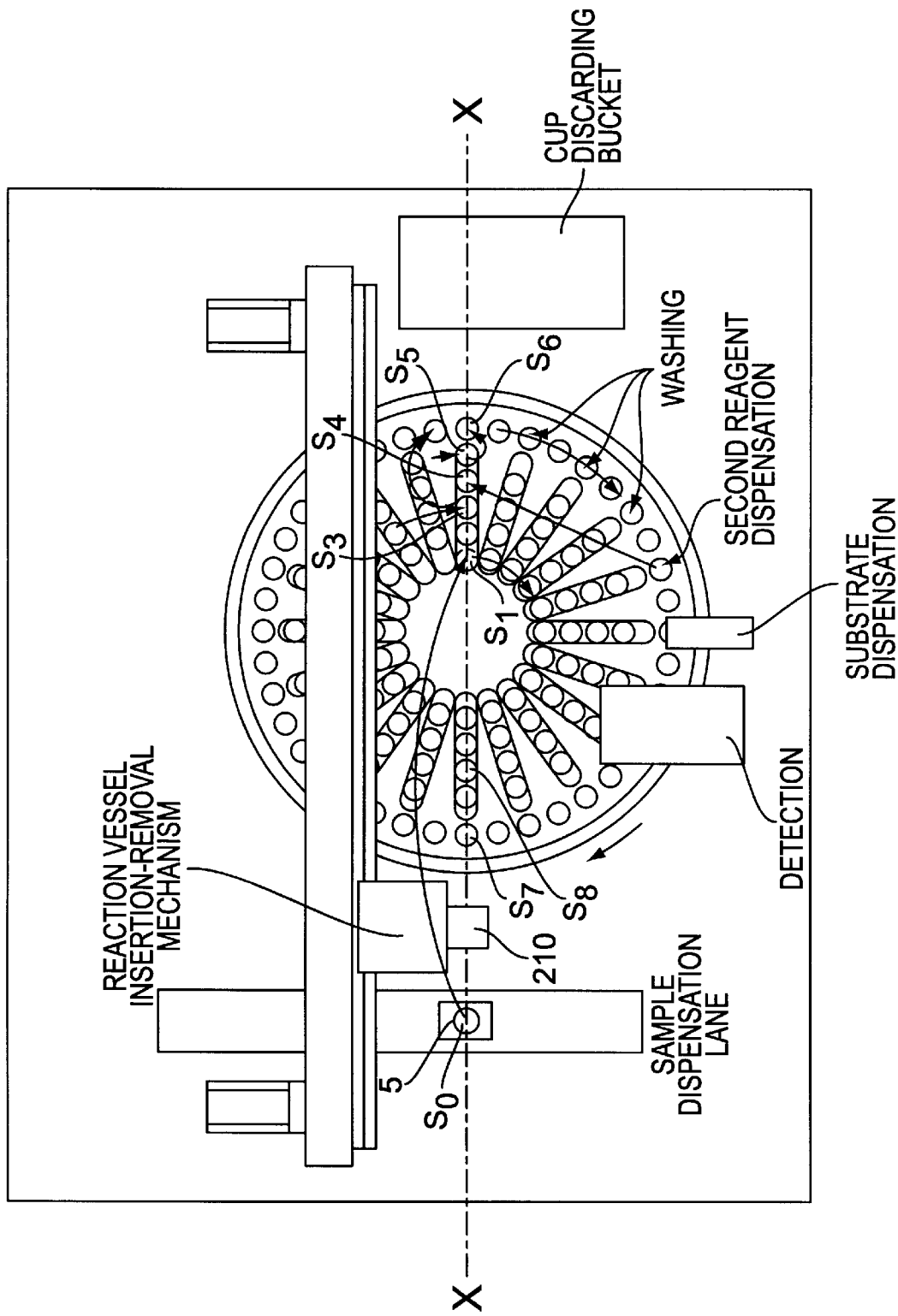
FIG. 13 illustrates movement of a reaction vessel in the apparatus of FIG. 10 in two-step treatment in 20 minutes.
Figure 14A:
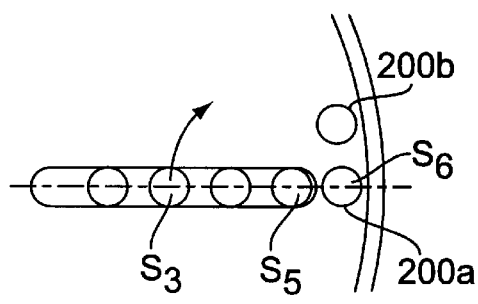
FIGS. 14A–14D illustrate in more detail the movement of the vessel in FIG. 13.
Figure 14B:
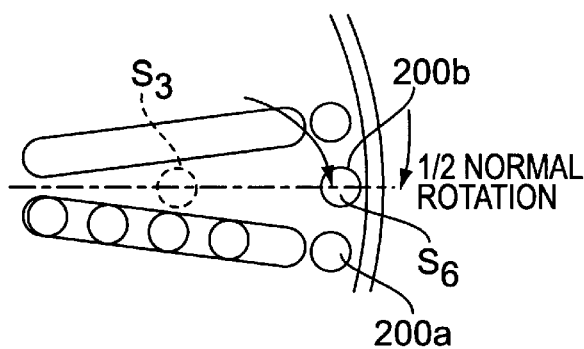
Figure 14C:
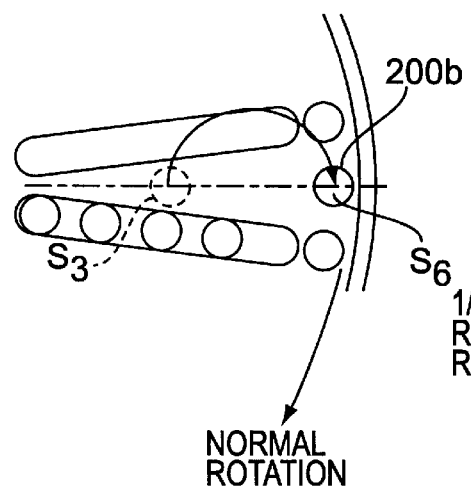
Figure 14D:
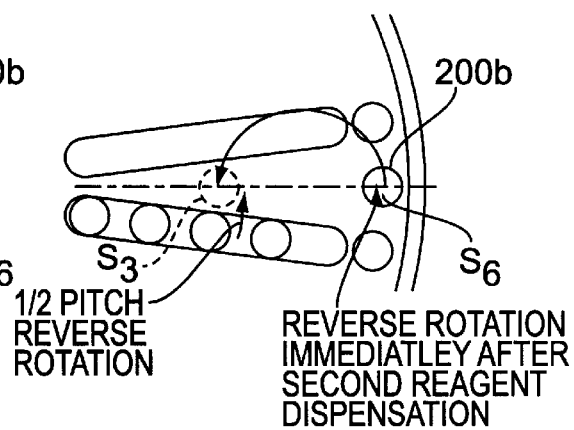

FIG. 13 illustrates the operation of only a two 40-minute step treatment by the movement of the reaction vessel. FIGS. 14A–14D shows supplementarily the detail thereof. The reaction vessel inserted to the position $S_1$ is conveyed to the position $S_3$ by two rotations of the disk. At this point of time, the reaction vessel is taken out from the slit (see FIG. 14A). Then the rotation disk 203 is turned by a ½ pitch (in the normal direction) to bring the vessel-holding hole 200b to the position $S_6$, and the reaction vessel is inserted to the vessel-holding hole 200b (see FIG. 14B). Thereafter, washing (intermediate washing) and the second reagent dispensation are conducted. The above treatments are shown collectively in FIG. 14C.

Immediately after dispensation of the second reagent to the reaction vessel, the rotation disk 203 is turned in the reverse direction and the reaction vessel is returned to the position $S_3$ in the slit by turning the rotation disk 203 further by ½ pitch. The vessel returning operation is reverse to the operation explained by reference to FIGS. 14A–14C. The vessel returning operation is shown collectively in FIG. 14D. The reaction vessel having been returned to the slit is conveyed immediately to the original position (the reverse turning start point after the second reagent dispensation). Instead, the reaction vessel after dispensation of the second reagent may be returned to the position $S_8$ in the slit 204 at the time when the reaction vessel has been conveyed to the position $S_7$ by normal rotation of the disk. Otherwise, the rotation disk is quickly turned in normal direction to bring the reaction vessel to the position $S_7$, the reaction vessel is returned to the position $S_8$ in the slit, and then the rotation disk is turned in the reverse direction to the original position. In these operations, when a linearly moving vessel insertion-removal mechanism is employed as in this embodiment, the rotation of the rotation disk is controlled not by intermittent one-pitch control but by ½ pitch (normal and reverse rotation), or by several pitches to move the vessel quickly to the opposing position, since the vessel-holding holes 200b are displaced respectively by ½ pitch from the slits.

When the reaction vessel returned to the slit 204 reaches the position $S_5$ after four rounds in total, it is transferred to the vessel-holding hole 200a at the position $S_6$, and subjected to the treatment of washing (final washing), substrate dispensation, and detection. As described above, the reaction vessel, after the operations of intermediate washing and the second reagent dispensation, may be returned from the position $S_6$ to the position $S_3$ by reverse turning of the disk, or may be returned from the position $S_7$ to $S_8$ by successive nearly half rotation of the disk in the normal rotation direction. Otherwise, it may be returned from the position $S_6$ to the position $S_4$ by successive intermittent nearly one rotation in the normal rotation direction. For these operations, the device may be equipped to turn the rotation disk 203 quickly in the normal or reverse direction. For the normal and reversal rotation of the rotation disk, the aforementioned margin of the spiral lane at the starting point or the terminal point is effective.

The one-step treatment and the two-step treatment described by reference to FIGS. 11–13 may be conducted in combination. A one 20-minute step treatment and another one 40-minute step treatment can be combinedly conducted by controlling the treatment processes of FIG. 11 and FIG. 12 for the respective reaction vessels by means of a microprocessor unit. A one-step treatment and a two-step treatment can be combinedly conducted by controlling the treatment processes of FIG. 11 and FIG. 13, FIG. 12 and FIG. 13, or FIG. 12 and FIG. 13 for the respective reaction vessels by control by means of a microprocessor unit. In these operations, the rotation disk 203 may be turned in the reverse rotation direction, as necessary.

The reaction apparatus of the present invention satisfies simultaneously the requirements for efficient process for measurement of a reaction in a short time with high precision without positional difference such as temperature distribution by conveying all the reaction vessel through the same route, and the requirement for miniaturization of the apparatus.

According to the present invention, reaction vessels for measurement items of different reaction times can be mixedly treated effectively without lowering the treatment efficiency.

When the present invention is applied to automatic analysis equipment utilizing an immune reaction, reaction vessels for different treatments, for example, of a one-step treatment not requiring intermediate washing and a two-step treatment requiring intermediate washing, can be treated in one and the same reaction apparatus without any inconvenience.

The reaction apparatus, in which reaction vessels are inserted into and removed from a turntable by a vessel insertion-removal mechanism moving linearly, can be made smaller in size and be simplified in mechanism owing to the simple constitution of the driving mechanism, and the production cost of the apparatus is reduced, which gives remarkable effects in industrial application.

The automatic analysis equipment can be made further simpler by arranging the vessel-holders for reaction vessels after the reaction along the periphery of the rotation plate since the conveying mechanism for the reaction can serve also for detection of the objective substance.

The apparatus utilizing the immune reaction can be made further simpler by arranging the vessel-holders for reaction vessels after the reaction along the periphery of the rotation plate since the treatments of intermediate washing and the final washing can be conducted by one and the same washing means.

By the above effects totally, the present invention provides the apparatus with a simple mechanism, high precision, a high performance at a low cost.

What is claimed is:

1. A reaction apparatus for automatic analysis comprising:
   a conveying mechanism to convey vessels containing an objective substance around a rotation center;
   said conveying mechanism comprising first guiding means for guiding the vessels along a spiral lane provided spirally on a first horizontal plane, and second guiding means for guiding the vessels along radial lanes provided radially on a second horizontal plane;
   said first guiding means and said second guiding means being placed concentrically and counterposed on different levels;
   the vessels being fixed into intersection points of said spiral lane and said radial lanes to control horizontal movement of the vessels by said spiral lane and said radial lanes; and
   the vessels being conveyed by rotation of at least one of said first guiding means and said second guiding means around the rotation center,
   further comprising means for automatically and simultaneously carrying vessels requiring different treatment periods which operates in conjunction with said first and second guiding means.

2. The reaction apparatus according to claim 1, wherein the vessels contain an objective biological sample in the physical form of a liquid, the apparatus operative for automatic immunoassay of a trace amount of an objective substance in said biological sample.

3. The reaction apparatus for automatic analysis according to claim 1, wherein said second guiding means comprises said radial lanes in plurality at constant angle intervals in radial directions toward the outer circumference of said spiral lane.

4. The reaction apparatus for automatic analysis according to claim 1, wherein at least one of said first guiding means and said second guiding means is provided in duplication separated by the other of said first guiding means and said second guiding means, so that corresponding lanes of the duplicated guiding means are placed to mirror each other.

5. A reaction apparatus for automatic analysis comprising:
   a conveying mechanism to convey vessels containing an objective substance around a rotation center;
   said conveying mechanism comprising first guiding means for guiding the vessels along a spiral lane provided spirally on a first horizontal plane, and second guiding means for guiding the vessels along the radial lanes provided radially on a second horizontal plane;
   said first guiding means and said second guiding means being placed concentrically and counterposed on different levels;
   the vessels being fixed into intersection points of the said spiral lane and said radial lanes to control horizontal movement of the vessels by said spiral lane and said radial lanes; and
   the vessels being conveyed by rotation of at least one of said first guiding means and said second guiding means around the rotation center,
   wherein said first guiding means is a fixed pedestal having said spiral lane formed in a groove or a vertical perforation hole, and said second guiding means is a rotation disk having said radial lanes formed in a vertical perforation and placed above said fixed pedestal of said first guiding means, further comprising means for automatically and simultaneously carrying vessels requiring different treatment periods which operates in conjunction with said first and second guiding means.

6. The reaction apparatus for automatic analysis according to claim 5, wherein a temperature control means is provided to control the surface temperature of said fixed pedestal.

7. The reaction apparatus for automatic analysis according to claim 1, wherein said second guiding means is a fixed pedestal having said radial lanes formed of a groove or a vertical perforation hole, and said first guiding means is a rotation disk having said spiral lane formed of a vertical perforation hole and placed above said fixed pedestal of said second guiding means.

8. The reaction apparatus for automatic analysis according to claim 7, wherein a temperature-control means is provided to control the surface temperature of said fixed pedestal.

9. The reaction apparatus for automatic analysis according to claim 1, wherein said first guiding means is a fixed plate having said spiral lane of a vertical perforation hole type;
   said second guiding means is a rotation disk having said radial lanes of a vertical perforation type and placed above or below said fixed plate of said first guiding means;
   a supporting plane below said first and second guiding means slidably supports the bottoms of the vessels inserted at the intersection points of said spiral lane and said radial lanes of vertical perforation hole type; and
   a temperature-control means controls the surface temperature of said supporting plane.

10. The reaction apparatus for automatic analysis according to claim 9, wherein said rotation disk as said second guiding means is arranged above said fixed disk as said first guiding means.

11. The reaction apparatus for automatic analysis according to claim 5, wherein said conveying mechanism receives vessels for a prescribed long-time treatment and vessels for short-time conveyance for a prescribed short-time treatment at a same receiving position, and releases the vessels for the short-time treatment at an intermediate point in a conveying route.

12. The reaction apparatus for automatic analysis according to claim 5, wherein said conveying mechanism receives a first kind of vessels for a prescribed long-time treatment and a second kind of vessels for short-time conveyance for a prescribed short-time treatment at separate receiving positions, and releases the first kind of vessels and the second kind of vessels from a same removal position.

13. The reaction apparatus for automatic analysis according to claim 5, wherein a plurality of vessel-holders are provided along the periphery of said rotation disk placed at an upper position.

14. The reaction apparatus for automatic analysis according to claims 13, wherein said plurality of vessel-holders are provided in a predetermined ratio to the number of radial lanes at a constant interval along the periphery of said rotation disk.

15. The reaction apparatus for automatic analysis according to claim 14, wherein said plurality of vessel-holders includes a first group of vessel-holders arranged in a single line along radially outer and inner sides of said radial lanes, and a second group of vessel-holders arranged between said first group of vessel-holders; and a set of vessel-holders comprising one holder each from said first and second groups receives a plurality of vessels inserted in one radial lane.

16. The reaction apparatus for automatic analysis according to claim 15, wherein said vessel-holders of the first group receive the vessels for final-step treatment, and said vessel-holders of the second group receive the vessels for an intermediate-step treatment.

17. The reaction apparatus for automatic analysis according to claim 13, further comprising a plurality of ports, wherein at least one of said plurality of ports is a reagent dispensation port for dispensing a reagent into the vessel, a substrate dispensation port for dispensing a substrate into the vessel, a washing port for washing the inside of the vessel, and a detection port for detecting the objective substance in the vessel, along a circulating route of said vessel-holders.

18. The reaction apparatus for automatic analysis according to claim 17, wherein the apparatus includes said reagent dispensation port for dispensing a reagent into the vessel, said substrate dispensation port for dispensing a substrate into the vessel, said washing port for washing the inside of the vessel and said detection port for detecting the objective substance in the vessel, along the circulating route of said vessel-holders.

19. The reaction apparatus for automatic analysis according to claim 13, wherein said means for automatically and simultaneously carrying vessels requiring different treatment periods includes a vessel insertion-removal means for inserting and removing the vessel into or from one of said intersection points of said spiral lane and said radial lanes, or said vessel-holder.

20. The reaction apparatus for automatic analysis according to claim 16, wherein said means for automatically and simultaneously carrying vessels requiring different treatment periods includes a vessel insertion-removal means for inserting and removing the vessel into or from one of said intersection points of said spiral lane and said radial lanes, and into or from said vessel-holders of the first group and the second groups, and has a control means for controlling said vessel insertion-removal means; and said vessel insertion-removal means is capable of transferring the vessel from one of said intersection points to said vessel-holder of the second group and returning the vessel again to the intersection point.

21. The reaction apparatus for automatic analysis according to claim 19, wherein said vessel insertion-removal means moves along the diameter line of said rotation disk between a prescribed vessel insertion position and a vessel removal position.

22. The reaction apparatus for automatic analysis according to claim 1, wherein the apparatus has a magnetic means for moving a magnetic body added into the vessel, said magnetic means comprising a a plurality of magnets arranged along said spiral lane.

23. The reaction apparatus for automatic analysis according to claim 13, wherein the apparatus has a magnetic means for moving a magnetic body added into the vessel, said magnetic means comprising a a plurality of magnets arranged along said spiral lane and said vessel-holders.

24. The reaction apparatus for automatic analysis according to claim 1, wherein the apparatus has a rotation drive-controlling means for controlling the rotation of said rotation disk for conveying the vessels.

25. The reaction apparatus for automatic analysis according to claim 24, wherein said rotation drive controlling means rotates said rotation disk in a normal direction and in a reverse direction.

26. The reaction apparatus for automatic analysis according to claim 1, further comprising a sample stocker carrying many vessels containing samples to be analyzed below, above, or on the same level as the reaction apparatus.

\* \* \* \* \*